(12) United States Patent
Seo

(10) Patent No.: US 8,913,242 B2
(45) Date of Patent: Dec. 16, 2014

(54) FINE PARTICLE MEASUREMENT DEVICE

(71) Applicant: Sony Corporation, Tokyo (JP)

(72) Inventor: Katsuhiro Seo, Kanagawa (JP)

(73) Assignee: Sony Corporation, Tokyo (JP)

( * ) Notice: Subject to any disclaimer, the term of this patent is extended or adjusted under 35 U.S.C. 154(b) by 8 days.

(21) Appl. No.: 13/828,054

(22) Filed: Mar. 14, 2013

(65) Prior Publication Data

US 2013/0242302 A1    Sep. 19, 2013

(30) Foreign Application Priority Data

Mar. 19, 2012    (JP) .................................. 2012-062192

(51) Int. Cl.
*G01N 15/02*    (2006.01)

(52) U.S. Cl.
CPC .................................. *G01N 15/0205* (2013.01)
USPC .......................................... 356/336; 356/337

(58) Field of Classification Search
USPC .................................. 356/335–343, 614–624
See application file for complete search history.

(56) References Cited

U.S. PATENT DOCUMENTS 5,272,354 A  *  12/1993  Kosaka .......................... 250/574
2010/0231925 A1 *  9/2010  Okuda et al. .................. 356/614

FOREIGN PATENT DOCUMENTS

| JP | 2010-190680 | 9/2010 |
| JP | 2012-026754 | 2/2012 |

* cited by examiner

*Primary Examiner* — Tri T Ton
(74) *Attorney, Agent, or Firm* — K&L Gates LLP

(57) ABSTRACT

A fine particle measurement device includes a 4f optical system in an optical path that causes a beam spot of a laser output from a light source to form an image with respect to fine particles.

6 Claims, 2 Drawing Sheets

FINE PARTICLE MEASUREMENT DEVICE

CROSS REFERENCES TO RELATED APPLICATIONS

The present application claims priority to Japanese Priority Patent Application JP 2012-062192 filed in the Japan Patent Office on Mar. 19, 2012, the entire content of which is hereby incorporated by reference.

BACKGROUND

The present disclosure relates to a fine particle measurement device. More specifically, the present disclosure relates to a fine particle measurement device which is capable of forming a beam spot of a sufficient size to irradiate fine particles with a laser at a uniform intensity.

Fine particle measurement devices that measure the characteristics of fine particles such as cells optically are known (for example, flow cytometers).

In flow cytometers, a sample liquid that includes cells is sent through a flow channel that is formed in flow cells or microchips, cells that flow inside of the flow channel are irradiated with a laser and the optical characteristics of the cells are measured by detecting the fluorescent light or scattered light that is generated from the cells using a detector. In addition, in flow cytometers, separation and collection of determined populations (groups) from the cells is performed when the results of measurement of optical characteristics and predetermined conditions are satisfied.

For example, in Japanese Unexamined Patent Application Publication No. 2010-190680, "a fine particle fractional collection device including a microchip in which a flow channel through which a liquid containing fine particles flows, and an orifice that expels the liquid that flows in the flow channel to the space outside the chip are disposed, a vibration element for discharging liquid by forming droplets in the orifice, charging means for applying a charge to discharged droplets, optical detecting means for detecting the optical characteristics of the fine particles that flow through the flow channel, paired electrodes arranged along the direction of movement of a droplet discharged to the space outside the chip and opposed with the moving droplet therebetween, and two or more vessels for collecting the droplets that pass between the paired electrodes" is disclosed as a microchip flow cytometer.

In flow cytometers, since cells that flow through a flow channel are irradiated by a laser at a uniform intensity, the beam spot of the laser that is concentrated on the flow channel is formed in a manner such that the spot diameter becomes a sufficient size with respect to the width of the flow channel. By forming the beam spot to be sufficiently large with respect to the width of the flow channel, it is possible to irradiate all of the cells with a laser at a uniform intensity since the beam spot is passed without being dependent on the flow position of each cell in the flow channel.

In Japanese Unexamined Patent Application Publication No. 2012-26754, a fine particle measurement device including a light irradiation system that transmits light from a light source through a phase level difference element that is divided into a plurality of regions and concentrates light on a sample flow in which fine particles flow is disclosed. In this fine particle measurement device, by generating phase differences between the wave surfaces of the light that is transmitted through each region of the phase level difference element, a beam spot that has a uniform distribution of intensity over a wide range is formed and the effective intensity of the laser with which the fine particles in the sample flow are irradiated is homogenized.

SUMMARY

In fine particle measurement devices, in order to form a beam spot with a large spot diameter, it is necessary to reduce the number of apertures (NA) of the imaging lens of the beam spot. In particular, in a case in which it is desirable to increase the spot diameter with respect to the wavelength of the laser, the NA becomes extremely small.

In a case in which the beam spot of the laser output from the light source is formed by a pair of imaging lenses, due to the circumstances mentioned above, setting the distance between the two imaging lenses to the sum of the focal point distances of the respective imaging lenses is a condition for favorable imaging. However, in a case in which the focal point distances of the respective imaging lenses is small, even if the two imaging lenses are disposed in contact with one another, the distance between the imaging lenses becomes larger than the sum of the focal point distances, and it is not possible to satisfy the abovementioned condition. For this reason, in fine particle measurement devices of the related art, it was difficult to form a beam spot with a desired spot diameter using an imaging lens with a small NA.

It is desirable to provide a fine particle measurement device which is capable of forming a beam spot that has a desired size.

According to an embodiment of the present disclosure, there is provided a fine particle measurement device which includes a 4f optical system in an optical path that causes a beam spot of a laser output from a light source to form an image with respect to fine particles. More specifically, the 4f optical system may be a relay lens system that is disposed between a first imaging lens and a second imaging lens that configure an imaging lens system of the beam spot, a first relay lens that configures the relay lens system may be disposed in a position in which the distance between the first relay lens and the first imaging lens is equal to the focal point distance of the first relay lens, a second relay lens that configures the relay lens system may be disposed in a position in which the distance between the second relay lens and the first relay lens is equal to the sum of the focal point distance of the first relay lens and the focal point distance of the second relay lens, and the distance between the second relay lens and the second imaging lens is equal to the focal point distance of the second relay lens.

In this fine particle measurement device, it may be possible to dispose an optical filter in one or more positions selected from between the first imaging lens and the first relay lens, between the first relay lens and the second relay lens, and between the second relay lens and the second imaging lens. The optical filter may be, for example, a mirror that reflects fluorescent light or scattered light that is generated from the fine particles as a result of irradiation with the laser, or a splitter that demultiplexes the laser.

The fine particle measurement device may include a detection system that detects the fluorescent light or scattered light that is reflected by the mirror, and may be configured to include an optical fiber that transmits the laser output from the light source and a lens system formed of the beam spot of the laser that is output from the optical fiber. It may be possible for the lens system formed of the beam spot to include a collimator lens and a pair of cylinder lenses.

In the present disclosure, the term "fine particles" includes a wide range such as biological fine particles such as cells and microorganisms, liposomes and the like, or synthetic particles such as latex particles and gel particles, particles for industrial use and the like.

The term biological fine particles includes various chromosomes, liposomes, mitochondria, organelles (cell organelles) and the like that are configured of various cells. The term cell includes animal cells (hematopoietic cells and the like) and plant cells. The term microorganism includes bacteria such as *E. Coli*, viruses such as tobacco mosaic virus and fungi such as yeast. Furthermore, the term biological fine particles may include biological polymers such as nucleic acids and proteins, or complexes thereof. In addition, particles for industrial use may be, for example, organic or inorganic polymer materials, metals or the like. The term organic polymers includes polystyrene, styrene-divinylbenzene, poly (methyl methacrylate) and the like. The term inorganic polymers includes glass, silica, magnetic materials and the like. The term metals includes gold colloids, aluminum. Generally, it is common for the shape of these fine particles to be spherical, but non-spherical forms are also possible and the size and quantity thereof is not particularly limited.

According to the embodiment of the present disclosure, it is possible to provide a fine particle measurement device that is capable of forming a beam spot that has a desired size.

Additional features and advantages are described herein, and will be apparent from the following Detailed Description and the figures.

DETAILED DESCRIPTION

Hereinafter, a favorable embodiment for achieving the present disclosure will be described with reference to the drawings. Additionally, the embodiment that is described below indicates an example of a representative embodiment of the present disclosure and does not limit the scope of the present disclosure. The description will be given in the following sequence.

1. Light Irradiation System
2. Detection System
1. Light Irradiation System

Figure 1:
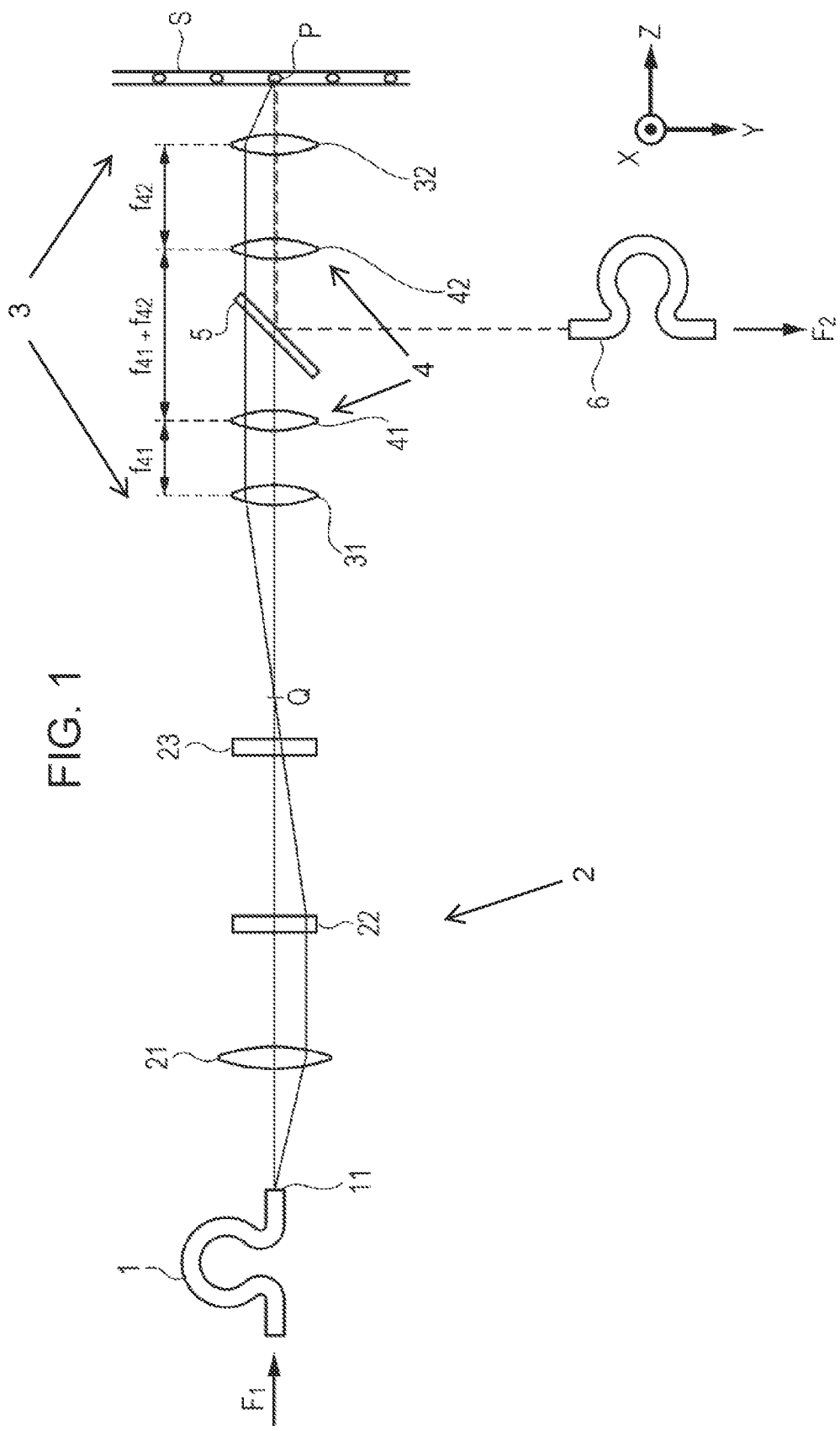
FIG. 1 is a view for describing the configuration of the light irradiation system and the detection system of a fine particle measurement device according to an embodiment of the present disclosure.

FIG. 1 is a schematic diagram that describes the configuration of the light irradiation system and the detection system of a fine particle measurement device according to an embodiment of the present disclosure.

Light output from a light source that is not shown in the drawings (refer to the solid line in FIG. 1) is transmitted using an optical fiber 1, and input into a lens system 2 that is formed of a collimator lens 21, a cylinder lens 22 and a cylinder lens 23. An arrow $F_1$ in the drawing indicates an input direction of light from the light source to the optical fiber 1. An existing light source of the related art may be used as the light source, but for example, it is possible to use a laser or an LED as appropriate. In addition, a plurality of light sources that respectively emit light of different wavelengths may be combined and used as the light source.

A lens system 2 forms a beam spot of light (also referred to as a "laser" below) that is output from an output terminal 11 of the optical fiber 1 in a position that is indicated by a Q symbol in the optical path. The collimator lens 21 configures a laser that is output from the output terminal 11 that forms a point light source as parallel light. The cylinder lens 22 and the cylinder lens 23 have lens powers in directions that are orthogonal to each other and function so as to form a beam spot of a predetermined size and shape (described in more detail later).

The beam spot that is formed in a position that is indicated by the Q symbol forms an image with respect to a sample flow S that contains fine particles P as a result of an imaging lens system 3 formed from a first imaging lens 31 and a second imaging lens 32. The sample flow S is a flow of a sample liquid that is sent through a flow channel that is formed in flow cells or microchips. The direction of travel of the laser from the output terminal 11 of the optical fiber 1 to the sample flow S is indicated by the forward direction of the Z axis in the drawing and the transfer direction of the sample flow S is indicated by the forward direction of the Y axis in the drawing.

In the fine particle measurement device according to an embodiment of the present disclosure, the optical fiber 1, the lens system 2 and the imaging lens system 3 configure an irradiation system for irradiating the fine particles P with the laser output from the light source. However, the optical fiber 1 is not a necessary component of the irradiation system.

A relay lens system 4 that is formed of a first relay lens 41 and a second relay lens 42 is disposed between the first imaging lens 31 and the second imaging lens 32. The imaging lens system 3 and the relay lens system 4 configure a so-called "4f optical system" and the first imaging lens 31, the first relay lens 41, the second relay lens 42 and the second imaging lens 32 are disposed to have the following positional relationships. That is, the first relay lens 41 is arranged in a position in which the distance between the first relay lens 41 and the first imaging lens 31 is equal to the focal point distance $f_{41}$ of the first relay lens 41. The second relay lens 42 is arranged in a position in which the distance between the second relay lens 42 and the first relay lens 41 is equal to the sum $(f_{41}+f_{42})$ of the focal point distance $f_{41}$ of the first relay lens 41 and the focal point distance $f_{42}$ of the second relay lens 42. In addition, the second relay lens 42 is arranged in a position in which the distance between the second relay lens 42 and the second imaging lens 32 is equal to the focal point distance $f_{42}$ of the second relay lens 42.

Using the focal point distance $f_{41}$ of the first relay lens 41 and the focal point distance $f_{42}$ of the second relay lens 42, the conversion magnification M of the spot diameter of the beam spot according to the 4f optical system is represented by a formula "$M=f_{42}/f_{41}$". Therefore, the beam spot formed in a position that is indicated by the Q symbol is imaged in the sample flow S as a beam spot in which the spot diameter is converted M times by the 4f optical system formed of the imaging lens system 3 and the relay lens system 4.

In a case in which the focal point distance $f_{41}$ of the first relay lens 41 and the focal point distance $f_{42}$ of the second relay lens 42 are equal, and the focal point distances of the first imaging lens 31 and the second imaging lens 32 are also equal, a beam spot of the same magnification as the beam spot formed in a position that is indicated by the Q symbol is imaged in the sample flow S.

Therefore, if a beam spot of a desired size and shape is formed in the position indicated by the Q symbol using the cylinder lens 22 and the cylinder lens 23 that have lens powers in directions that are orthogonal to each other, it is possible to irradiate the sample flow S with a beam spot of the same size and shape. In addition, it is also possible to suppress aberrations in the 4f optical system to a small amount.

Figure 2:
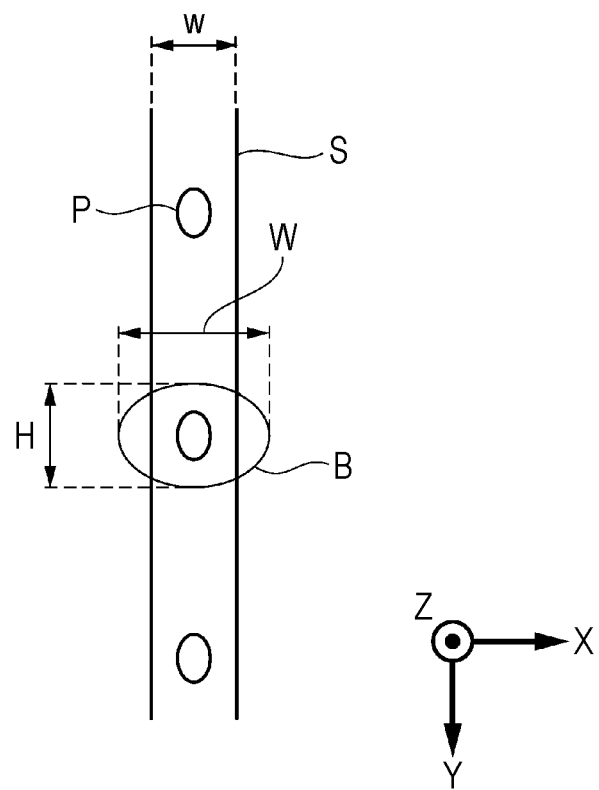
FIG. 2 is a view that describes an example of a suitable size and shape of the beam spot that is imaged in a sample flow that contains fine particles.

FIG. 2 shows an example of a suitable size and shape of the beam spot that is imaged on a sample flow S that contains fine particles P.

It is preferable that the beam spot B that is imaged in the sample flow S have a shape that is wide in the width direction of the sample flow S. In addition, in the beam spot B, it is preferable that the spot diameter of the same direction be equal to or larger than the width of the sample flow S. More specifically, if the sending direction of the sample flow S is set as the forward direction of the Y axis and the width direction of sample flow S that is orthogonal thereto is set as the X axis direction, it is preferable that the beam spot B have an elliptical shape in which the spot diameter W of the X axis direction is larger than the spot diameter H of the Y axis direction. In addition, it is preferable that the spot diameter W of the beam spot B have a length that is greater than or equal to the width w of the sample flow S. Additionally, the width w corresponds to a width of the flow channel of a flow cell of a microchip through which the sample flow S is sent.

By imaging a beam spot B that is configured to have such a size and shape in a sample flow S, it is possible to irradiate all of the fine particles P with a laser of a uniform intensity since the beam spot B is passed without being dependent on the flow positions of the fine particles P in the sample flow S.

The formation of the beam spot B may be performed by applying a lens power of the X axis direction to the cylinder lens 22 and a lens power of the Y axis direction to the cylinder lens 23, and adjusting the spot diameters of the X axis direction and the Y axis direction of the beam spot that is formed in the position which is indicated by the Q symbol.

In a case in which the beam spot that is formed in the position which is indicated by the Q symbol is imaged in the sample flow S at the same magnification, the laser power may be set such that the spot diameters of the X axis direction and the Y axis direction of the beam spot that is formed in the position which is indicated by the Q symbol satisfy the abovementioned suitable size and shape.

In addition, in a case in which the beam spot that is formed in the position which is indicated by the Q symbol is imaged in the sample flow S at a different magnification (magnification M, where M is not 1), the laser power may be set such that the spot diameters of the X axis direction and the Y axis direction of the beam spot that is formed in the position which is indicated by the Q symbol satisfy the abovementioned suitable size and shape after magnification by M.

The NAs of the convergent light of the cylinder lens 22 and the cylinder lens 23 are, for example, respectively set as $0.001/\pi$ and $0.01/\pi$. In such a case, if the wavelength of the laser is set to 0.5 μm, a beam spot in which the spot diameters of the X axis direction and the Y axis direction are 100 and 10 μm respectively, is formed in the position indicated by the Q symbol.

2. Detection System

Fluorescent light and light scattered (refer to the dotted line in FIG. 1) to the rear that is generated from the fine particles P as a result of irradiation with the laser is reflected by a mirror 5, and transmitted to a detector that is not shown in the drawings using an optical fiber 6. The mirror 5 and the optical fiber 6 configure a detection system for detecting detection target light that is generated by the fine particles P. However, the optical fiber 6 is not a necessary component of the detection system.

In the 4f optical system in which the relay lens system 4 is disposed between the imaging lens system 3, in comparison with a case in which only an imaging lens system 3 is arranged, it is possible to have a greater distance between the first imaging lens 31 and the second imaging lens 32. For this reason, as shown in the drawings, it is easy to insert an optical filter such as the mirror 5 between the first relay lens 41 and the second relay lens 42.

An area imaging element such as a photo multiplier tube (PMT), a photodiode, a CCD, a CMOS element or the like is adopted in the detector that detects fluorescent light and the like reflected by the mirror 5. The fluorescent light that is to be detected may be fluorescent light generated from fine particles P or a fluorescent light pigment that is labeled in the fine particles P as a result of irradiation with the laser. The detected fluorescent light is converted into an electronic signal and used for optical characteristic determination of the fine particles P.

In the present disclosure, in the fine particle measurement device, as described above, since it is possible to irradiate fine particles P in a sample flow S with a laser of a uniform intensity without being dependent on the flow positions thereof, it is possible to accurately measure the optical characteristics of the fine particles P.

The mirror 5 can be inserted in an arbitrary position in the 4f optical system formed from an imaging lens system 3 and a relay lens system 4. For example, the mirror 5 may be disposed between the first imaging lens 31 and the first relay lens 41 or between the second relay lens 42 the second imaging lens 32. In addition, in place of the mirror 5, an optical filter such as a splitter that demultiplexes the laser may be inserted. By disposing a splitter and providing a detector that detects the laser that is demultiplexed, it is possible to monitor the amount of light of the laser that is output from the light source.

Additionally, although it is not shown in the drawings, the fine particle measurement device according to an embodiment of the present disclosure may be provided with a configuration for detecting light scattered to the front that is generated from the fine particles P as a result of irradiation with the laser.

It is possible for the fine particle measurement device according to an embodiment of the present disclosure to have the following configurations.

(1) A fine particle measurement device including a 4f optical system in an optical path that causes a beam spot of a laser output from a light source to form an image with respect to fine particles.

(2) The fine particle measurement device according to (1), in which the 4f optical system is a relay lens system that is disposed between a first imaging lens and a second imaging lens that configure an imaging lens system of the beam spot, a first relay lens that configures the relay lens system is disposed in a position in which the distance between the first relay lens and the first imaging lens is equal to the focal point distance of the first relay lens, a second relay lens that configures the relay lens system is disposed in a position in which the distance between the second relay lens and the first relay lens is equal to the sum of the focal point distance of the first relay lens and the focal point distance of the second relay lens, and the distance between the second relay lens and the second imaging lens is equal to the focal point distance of the second relay lens.

(3) The fine particle measurement device according to (2), in which an optical filter is disposed in one or more positions selected from between the first imaging lens and the first relay lens, between the first relay lens and the second relay lens, and between the second relay lens and the second imaging lens.

(4) The fine particle measurement device according to (3), in which the optical filter is a mirror that reflects fluorescent light or scattered light that is generated from the fine particles as a result of irradiation with the laser, or a splitter that demultiplexes the laser.

(5) The fine particle measurement device according to (4), further including a detection system that detects the fluorescent light or scattered light that is reflected by the mirror.

(6) The fine particle measurement device according to any one of (1) to (5), further including an optical fiber that transmits the laser output from the light source and a lens system formed of the beam spot of the laser that is output from the optical fiber.

(7) The fine particle measurement device according to (6), in which the lens system formed of the beam spot includes a collimator lens and a pair of cylinder lenses.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A fine particle measurement device comprising:
    a 4f optical system in an optical path that causes a beam spot of a laser output from a light source to form an image with respect to fine particles,
    wherein the 4f optical system is a relay lens system that is disposed between a first imaging lens and a second imaging lens that configure an imaging lens system of the beam spot,
    wherein a first relay lens that configures the relay lens system is disposed in a position in which the distance between the first relay lens and the first imaging lens is equal to the focal point distance of the first relay lens,
    wherein a second relay lens that configures the relay lens system is disposed in a position in which the distance between the second relay lens and the first relay lens is equal to the sum of the focal point distance of the first relay lens and the focal point distance of the second relay lens, and the distance between the second relay lens and the second imaging lens is equal to the focal point distance of the second relay lens,
    wherein an optical filter is disposed in one or more positions selected from between the first imaging lens and the first relay lens, between the first relay lens and the second relay lens, and between the second relay lens and the second imaging lens, and
    wherein the optical filter is a mirror that reflects fluorescent light or scattered light that is generated from the fine particles as a result of irradiation with the laser, or a splitter that demultiplexes the laser.

2. The fine particle measurement device according to claim 1, further comprising:
    a detection system that detects the fluorescent light or scattered light that is reflected by the mirror.

3. The fine particle measurement device according to claim 2, further comprising:
    an optical fiber that transmits the laser output from the light source and a lens system formed of the beam spot of the laser that is output from the optical fiber.

4. The fine particle measurement device according to claim 3, wherein the lens system formed of the beam spot includes a collimator lens and a pair of cylinder lenses.

5. The fine particle measurement device according to claim 1 further comprising an optical fiber that transmits the laser output from the light source and a lens system formed of the beam spot of the laser that is output from the optical fiber.

6. The fine particle measurement device according to claim 5, wherein the lens system formed of the beam spot includes a collimator lens and a pair of cylinder lenses.

* * * * *